United States Patent
Higgins et al.

(10) Patent No.: US 11,926,855 B2
(45) Date of Patent: Mar. 12, 2024

(54) FEED COMPOSITION SUPPLEMENTED WITH A PROTEASE COMBINATION

(71) Applicant: Kerry Luxembourg S.à.r.l., Luxembourg (LU)

(72) Inventors: Niall Higgins, Nass (IE); Jacques Georis, Heron (BE); Sara Llamas Moya, Eadestown (IE); Nathan Marshall, Warrington (GB); Derek Carr, Dublin (IE); Rachel Maloney, Broadway (IE); Laura Guaras, Novallas Zaragoza (ES)

(73) Assignee: Kerry Group Services International Limited, Tralee (IE)

( * ) Notice: Subject to any disclaimer, the term of this patent is extended or adjusted under 35 U.S.C. 154(b) by 81 days.

(21) Appl. No.: 17/128,960

(22) Filed: Dec. 21, 2020

(65) Prior Publication Data
US 2022/0061354 A1  Mar. 3, 2022

Related U.S. Application Data

(60) Provisional application No. 63/071,818, filed on Aug. 28, 2020.

(51) Int. Cl.
| | |
|---|---|
| *C12N 9/26* | (2006.01) |
| *A23K 10/14* | (2016.01) |
| *A23K 50/75* | (2016.01) |
| *C12N 9/48* | (2006.01) |
| *C12N 9/64* | (2006.01) |

(52) U.S. Cl.
CPC ............ *C12N 9/6489* (2013.01); *A23K 10/14* (2016.05); *A23K 50/75* (2016.05); *C12N 9/2411* (2013.01); *C12N 9/485* (2013.01); *C12N 9/6424* (2013.01)

(58) Field of Classification Search
CPC .. C12N 9/2411; C12N 9/6424; C12N 9/6489; C12N 9/485
See application file for complete search history.

(56) References Cited

U.S. PATENT DOCUMENTS

| | | | | |
|---|---|---|---|---|
| 2008/0260894 A1* | 10/2008 | Lim | ....................... | A23K 50/30 426/2 |
| 2014/0234279 A1* | 8/2014 | Millan | .................... | A61P 43/00 424/93.46 |

FOREIGN PATENT DOCUMENTS

| | | | | | |
|---|---|---|---|---|---|
| WO | WO-9605295 A2 | * | 2/1996 | ............. | C11D 3/386 |
| WO | WO-2007044993 A2 | * | 4/2007 | ............... | C11D 1/02 |
| WO | WO-2017083196 A1 | * | 5/2017 | ............. | A23K 10/18 |

* cited by examiner

*Primary Examiner* — Yong D Pak
(74) *Attorney, Agent, or Firm* — Sughrue Mion, PLLC

(57) ABSTRACT

An enzyme composition containing a protease combination or a protease mixture having neutral metalloprotease and serine alkaline protease activity, and an amylase. Feed compositions, additives and formulations containing the enzyme composition in methods for improving digestibility of proteins in an animal diet or animal feed, as well as optimizing the nutritional value of an animal diet or animal feed.

20 Claims, 3 Drawing Sheets

Specification includes a Sequence Listing.

SEQUENCE LISTING

<160> NUMBER OF SEQ ID NOS: 7

<210> SEQ ID NO 1
<211> LENGTH: 374

<212> TYPE: PRT
<213> ORGANISM: Bacillus amyloliquefaciens

<400> SEQUENCE: 1

```
Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
50                  55                  60

Gly Lys Val Gln Lys Gln Phe Lys Tyr Val Asp Ala Ala Arg Leu Gln
65                  70                  75                  80

Leu His Met Lys Lys Asp Pro Ser Val Ala Tyr Val Glu Glu Asp His
                85                  90                  95

Val Ala His Ala Tyr Ala Gln Ser Met Pro Tyr Gly Val Ser Gln Ile
            100                 105                 110

Lys Ala Pro Ala Leu His Ser Gln Gly Tyr Thr Gly Ser Asn Val Lys
        115                 120                 125

Val Ala Val Ile Asp Ser Gly Ile Asp Ser Ser His Pro Asp Leu Lys
130                 135                 140

Val Ala Gly Gly Ala Ser Met Val Pro Ser Glu Thr Asn Pro Phe Gln
145                 150                 155                 160

Asp Asn Asn Ser His Gly Thr His Val Ala Gly Thr Val Ala Ala Leu
                165                 170                 175

Asn Asn Ser Ile Gly Val Leu Gly Val Ala Pro Ser Ala Ser Leu Tyr
            180                 185                 190

Ala Val Lys Val Leu Gly Ala Asp Gly Ser Gly Gln Tyr Ser Trp Ile
        195                 200                 205

Ile Asn Gly Ile Glu Trp Ala Ile Ala Asn Asn Met Asp Val Ile Asn
210                 215                 220

Met Ser Leu Gly Gly Thr Phe Trp Phe Cys Cys Phe Lys Ser Ala Val
225                 230                 235                 240

Glu Glu Ala Trp Asn Ala Gly Ile Val Val Cys Val Ala Ala Gly Asn
                245                 250                 255

Ser Gly Pro Gly Ser Thr Asn Met Gly Tyr Pro Gly Lys Tyr Pro Ser
            260                 265                 270

Val Ile Ala Val Gly Ala Val Asp Ser Ser Asn Gln Arg Ala Ser Phe
        275                 280                 285

Ser Ser Val Gly Pro Glu Leu Asp Val Met Ala Pro Gly Val Ser Ile
290                 295                 300

Gln Ser Thr Leu Pro Gly Asn Lys Tyr Gly Ala Tyr Asn Gly Thr Ser
305                 310                 315                 320

Met Ala Ser Pro His Val Ala Gly Ala Ala Leu Ile Leu Ser Lys
                325                 330                 335

His Pro Asn Trp Thr Asn Thr Gln Val Arg Ser Ser Leu Glu Asn Thr
            340                 345                 350

Thr Thr Lys Leu Gly Asp Ser Phe Tyr Tyr Gly Lys Gly Leu Ile Asn
        355                 360                 365

Val Gln Ala Ala Ala Gln
    370
```

<210> SEQ ID NO 2

```
<211> LENGTH: 521
<212> TYPE: PRT
<213> ORGANISM: Bacillus amyloliquefaciens

<400> SEQUENCE: 2

Met Gly Leu Gly Lys Lys Leu Ser Val Ala Val Ala Ala Ser Phe Met
1               5                   10                  15

Ser Leu Thr Ile Ser Leu Pro Gly Val Gln Ala Ala Glu Asn Pro Gln
            20                  25                  30

Leu Lys Glu Asn Leu Thr Asn Phe Val Pro Lys His Ser Leu Val Gln
        35                  40                  45

Ser Glu Leu Pro Ser Val Ser Asp Lys Ala Ile Lys Gln Tyr Leu Lys
    50                  55                  60

Gln Asn Gly Lys Val Phe Lys Gly Asn Pro Ser Glu Arg Leu Lys Leu
65                  70                  75                  80

Ile Asp Gln Thr Thr Asp Asp Leu Gly Tyr Lys His Phe Arg Tyr Val
                85                  90                  95

Pro Val Val Asn Gly Val Pro Val Lys Asp Ser Gln Val Ile Ile His
            100                 105                 110

Val Asp Lys Ser Asn Asn Val Tyr Ala Ile Asn Gly Glu Leu Asn Asn
        115                 120                 125

Asp Val Ser Ala Lys Thr Ala Asn Ser Lys Lys Leu Ser Ala Asn Gln
    130                 135                 140

Ala Leu Asp His Ala Tyr Lys Ala Ile Gly Lys Ser Pro Glu Ala Val
145                 150                 155                 160

Ser Asn Gly Thr Val Ala Asn Lys Asn Lys Ala Glu Leu Lys Ala Ala
                165                 170                 175

Ala Thr Lys Asp Gly Lys Tyr Arg Leu Ala Tyr Asp Val Thr Ile Arg
            180                 185                 190

Tyr Ile Glu Pro Glu Pro Ala Asn Trp Glu Val Thr Val Asp Ala Glu
        195                 200                 205

Thr Gly Lys Ile Leu Lys Lys Gln Asn Lys Val Glu His Ala Ala Thr
    210                 215                 220

Thr Gly Thr Gly Thr Thr Leu Lys Gly Lys Thr Val Ser Leu Asn Ile
225                 230                 235                 240

Ser Ser Glu Ser Gly Lys Tyr Val Met Arg Asp Leu Ser Lys Pro Thr
                245                 250                 255

Gly Thr Gln Ile Ile Thr Tyr Asp Leu Gln Asn Arg Glu Tyr Asn Leu
            260                 265                 270

Pro Gly Thr Leu Val Ser Ser Thr Thr Asn Gln Phe Thr Thr Ser Ser
        275                 280                 285

Gln Arg Ala Ala Val Asp Ala His Tyr Asn Leu Gly Lys Val Tyr Asp
    290                 295                 300

Tyr Phe Tyr Gln Lys Phe Asn Arg Asn Ser Tyr Asp Asn Lys Gly Gly
305                 310                 315                 320

Lys Ile Val Ser Ser Val His Tyr Gly Ser Arg Tyr Asn Asn Ala Ala
                325                 330                 335

Trp Ile Gly Asp Gln Met Ile Tyr Gly Asp Gly Asp Gly Ser Phe Phe
            340                 345                 350

Ser Pro Leu Ser Gly Ser Met Asp Val Thr Ala His Glu Met Thr His
        355                 360                 365

Gly Val Thr Gln Glu Thr Ala Asn Leu Asn Tyr Glu Asn Gln Pro Gly
    370                 375                 380

Ala Leu Asn Glu Ser Phe Ser Asp Val Phe Gly Tyr Phe Asn Asp Thr
```

```
            385                 390                 395                 400
Glu Asp Trp Asp Ile Gly Glu Asp Ile Thr Val Ser Gln Pro Ala Leu
                405                 410                 415

Arg Ser Leu Ser Asn Pro Thr Lys Tyr Gly Gln Pro Asp Asn Phe Lys
            420                 425                 430

Asn Tyr Lys Asn Leu Pro Asn Thr Asp Ala Gly Asp Tyr Gly Gly Val
        435                 440                 445

His Thr Asn Ser Gly Ile Pro Asn Lys Ala Ala Tyr Asn Thr Ile Thr
    450                 455                 460

Lys Ile Gly Val Asn Lys Ala Glu Gln Ile Tyr Tyr Arg Ala Leu Thr
465                 470                 475                 480

Val Tyr Leu Thr Pro Ser Ser Thr Phe Lys Asp Ala Lys Ala Ala Leu
                485                 490                 495

Ile Gln Ser Ala Arg Asp Leu Tyr Gly Ser Gln Asp Ala Ala Ser Val
            500                 505                 510

Glu Ala Ala Trp Asn Ala Val Gly Leu
            515                 520

<210> SEQ ID NO 3
<211> LENGTH: 492
<212> TYPE: PRT
<213> ORGANISM: Bacillus amyloliquefaciens

<400> SEQUENCE: 3

Ser Thr Pro Trp Trp Lys Lys Ala Ala Val Tyr Gln Ile Tyr Met Gln
1               5                   10                  15

Tyr Phe Glu Trp Tyr Thr Pro Asn Asp Gly Gln His Trp Lys Arg Leu
            20                  25                  30

Gln Asn Asp Ala Glu His Leu Ser Asp Ile Gly Ile Thr Ala Val Trp
        35                  40                  45

Ile Pro Pro Ala Tyr Lys Gly Leu Ser Gln Ser Asp Asn Gly Tyr Gly
    50                  55                  60

Pro Tyr Asp Leu Tyr Asp Leu Gly Glu Phe Gln Gln Lys Gly Thr Val
65                  70                  75                  80

Arg Thr Lys Tyr Gly Thr Lys Ser Glu Leu Gln Asp Ala Ile Gly Ser
                85                  90                  95

Leu His Ser Arg Asn Val Gln Val Tyr Gly Asp Val Val Leu Asn His
            100                 105                 110

Lys Ala Gly Ala Asp Ala Thr Glu Asp Val Thr Ala Val Glu Val Asn
        115                 120                 125

Pro Ala Asn Arg Asn Gln Val Thr Ser Glu Glu Tyr Gln Ile Lys Ala
    130                 135                 140

Trp Thr Asp Phe Arg Phe Pro Gly Arg Gly Asn Thr Tyr Ser Asp Phe
145                 150                 155                 160

Lys Trp His Trp Tyr His Phe Asp Gly Ala Asp Trp Asp Glu Ser Arg
                165                 170                 175

Lys Ile Ser Arg Ile Phe Lys Phe Arg Gly Glu Gly Lys Ala Trp Asp
            180                 185                 190

Trp Glu Val Ser Ser Glu Asn Gly Asn Tyr Asp Tyr Leu Met Tyr Ala
        195                 200                 205

Asp Val Asp Tyr Asp His Pro Asp Val Val Ala Glu Thr Lys Lys Trp
    210                 215                 220

Gly Ile Trp Tyr Ala Asn Glu Leu Ser Leu Asp Gly Phe Arg Ile Asp
225                 230                 235                 240
```

```
Ala Ala Lys His Ile Lys Phe Ser Phe Leu Arg Asp Trp Val Gln Ala
            245                 250                 255

Val Arg Gln Ala Thr Gly Lys Glu Met Phe Thr Val Ala Glu Tyr Trp
        260                 265                 270

Gln Asn Asn Ala Gly Lys Leu Glu Asn Tyr Leu Asn Lys Thr Ser Phe
    275                 280                 285

Asn Gln Ser Val Phe Asp Val Pro Leu His Phe Asn Leu Gln Ala Ala
290                 295                 300

Ser Ser Gln Gly Gly Tyr Asp Met Arg Arg Leu Leu Asp Gly Thr
305                 310                 315                 320

Val Val Ser Arg His Pro Glu Lys Ala Val Thr Phe Val Glu Asn His
            325                 330                 335

Asp Thr Gln Pro Gly Gln Ser Leu Glu Ser Thr Val Gln Thr Trp Phe
        340                 345                 350

Lys Pro Leu Ala Tyr Ala Phe Ile Leu Thr Arg Glu Ser Gly Tyr Pro
    355                 360                 365

Gln Val Phe Tyr Gly Asp Met Tyr Gly Thr Lys Gly Thr Ser Pro Lys
370                 375                 380

Glu Ile Pro Ser Leu Lys Asp Asn Ile Glu Pro Ile Leu Lys Ala Arg
385                 390                 395                 400

Lys Glu Tyr Ala Tyr Gly Pro Gln His Asp Tyr Ile Asp His Pro Asp
            405                 410                 415

Val Ile Gly Trp Thr Arg Glu Gly Asp Ser Ser Ala Ala Lys Ser Gly
        420                 425                 430

Leu Ala Ala Leu Ile Met Asp Gly Pro Gly Gly Ser Lys Arg Met Tyr
    435                 440                 445

Ala Gly Leu Lys Asn Ala Gly Glu Thr Trp Tyr Asp Ile Thr Gly Asn
450                 455                 460

Arg Ser Asp Thr Val Lys Ile Gly Ser Asp Gly Trp Gly Glu Phe His
465                 470                 475                 480

Val Asn Asp Gly Ser Val Ser Ile Tyr Val Gln Lys
            485                 490

<210> SEQ ID NO 4
<211> LENGTH: 382
<212> TYPE: PRT
<213> ORGANISM: Bacillus amyloliquefaciens

<400> SEQUENCE: 4

Met Arg Gly Lys Lys Val Trp Ile Ser Leu Leu Phe Ala Leu Ala Leu
1               5                   10                  15

Ile Phe Thr Met Ala Phe Gly Ser Thr Ser Ser Ala Gln Ala Ala Gly
            20                  25                  30

Lys Ser Asn Gly Glu Lys Lys Tyr Ile Val Gly Phe Lys Gln Thr Met
        35                  40                  45

Ser Thr Met Ser Ala Ala Lys Lys Lys Asp Val Ile Ser Glu Lys Gly
    50                  55                  60

Gly Lys Val Gln Lys Gln Phe Lys Tyr Val Asp Ala Ala Ser Ala Thr
65                  70                  75                  80

Leu Asn Glu Lys Ala Val Lys Glu Leu Lys Lys Asp Pro Ser Val Ala
            85                  90                  95

Tyr Val Glu Glu Asp His Val Ala His Ala Tyr Ala Gln Ser Val Pro
        100                 105                 110

Tyr Gly Val Ser Gln Ile Lys Ala Pro Ala Leu His Ser Gln Gly Tyr
    115                 120                 125
```

```
Thr Gly Ser Asn Val Lys Val Ala Val Ile Asp Ser Gly Ile Asp Ser
    130                 135                 140

Ser His Pro Asp Leu Lys Val Ala Gly Gly Ala Ser Met Val Pro Ser
145                 150                 155                 160

Glu Thr Asn Pro Phe Gln Asp Asn Asn Ser His Gly Thr His Val Ala
                165                 170                 175

Gly Thr Val Ala Ala Leu Asn Asn Ser Ile Gly Val Leu Gly Val Ala
                180                 185                 190

Pro Ser Ala Ser Leu Tyr Ala Val Lys Val Leu Gly Ala Asp Gly Ser
            195                 200                 205

Gly Gln Tyr Ser Trp Ile Ile Asn Gly Ile Glu Trp Ala Ile Ala Asn
    210                 215                 220

Asn Met Asp Val Ile Asn Met Ser Leu Gly Gly Pro Ser Gly Ser Ala
225                 230                 235                 240

Ala Leu Lys Ala Ala Val Asp Lys Ala Val Ala Ser Gly Val Val Val
                245                 250                 255

Val Ala Ala Ala Gly Asn Glu Gly Thr Ser Gly Ser Ser Ser Thr Val
                260                 265                 270

Gly Tyr Pro Gly Lys Tyr Pro Ser Val Ile Ala Val Gly Ala Val Asp
            275                 280                 285

Ser Ser Asn Gln Arg Ala Ser Phe Ser Ser Val Gly Pro Glu Leu Asp
    290                 295                 300

Val Met Ala Pro Gly Val Ser Ile Gln Ser Thr Leu Pro Gly Asn Lys
305                 310                 315                 320

Tyr Gly Ala Tyr Asn Gly Thr Ser Met Ala Ser Pro His Val Ala Gly
                325                 330                 335

Ala Ala Ala Leu Ile Leu Ser Lys His Pro Asn Trp Thr Asn Thr Gln
            340                 345                 350

Val Arg Ser Ser Leu Glu Asn Thr Thr Thr Lys Leu Gly Asp Ser Phe
    355                 360                 365

Tyr Tyr Gly Lys Gly Leu Ile Asn Val Gln Ala Ala Gln
            370                 375                 380

<210> SEQ ID NO 5
<211> LENGTH: 521
<212> TYPE: PRT
<213> ORGANISM: Bacillus amyloliquefaciens

<400> SEQUENCE: 5

Met Gly Leu Gly Lys Lys Leu Ser Val Ala Val Ala Ala Ser Phe Met
1               5                   10                  15

Ser Leu Thr Ile Ser Leu Pro Gly Val Gln Ala Glu Asn Pro Gln
                20                  25                  30

Leu Lys Glu Asn Leu Thr Asn Phe Val Pro Lys His Ser Leu Val Gln
            35                  40                  45

Ser Glu Leu Pro Ser Val Ser Asp Lys Ala Ile Lys Gln Tyr Leu Lys
        50                  55                  60

Gln Asn Gly Lys Val Phe Lys Gly Asn Pro Ser Glu Arg Leu Lys Leu
65                  70                  75                  80

Ile Asp Gln Thr Thr Asp Leu Gly Tyr Lys His Phe Arg Tyr Val
                85                  90                  95

Pro Val Val Asn Gly Val Pro Val Lys Asp Ser Gln Val Ile Ile His
                100                 105                 110

Val Asp Lys Ser Asn Asn Val Tyr Ala Ile Asn Gly Glu Leu Asn Asn
```

```
            115                 120                 125
Asp Val Ser Ala Lys Thr Ala Asn Ser Lys Leu Ser Ala Asn Gln
130                 135                 140

Ala Leu Asp His Ala Tyr Lys Ala Ile Gly Lys Ser Pro Glu Ala Val
145                 150                 155                 160

Ser Asn Gly Thr Val Ala Asn Lys Asn Lys Ala Glu Leu Lys Ala Ala
                165                 170                 175

Ala Thr Lys Asp Gly Lys Tyr Arg Leu Ala Tyr Asp Val Thr Ile Arg
            180                 185                 190

Tyr Ile Glu Pro Glu Pro Ala Asn Trp Glu Val Thr Val Asp Ala Glu
        195                 200                 205

Thr Gly Lys Ile Leu Lys Lys Gln Asn Lys Val Glu His Ala Ala Thr
    210                 215                 220

Thr Gly Thr Gly Thr Thr Leu Lys Gly Lys Thr Val Ser Leu Asn Ile
225                 230                 235                 240

Ser Ser Glu Ser Gly Lys Tyr Val Leu Arg Asp Leu Ser Lys Pro Thr
                245                 250                 255

Gly Thr Gln Ile Ile Thr Tyr Asp Leu Gln Asn Arg Glu Tyr Asn Leu
            260                 265                 270

Pro Gly Thr Leu Val Ser Ser Thr Asn Gln Phe Thr Ser Ser
        275                 280                 285

Gln Arg Ala Ala Val Asp Ala His Tyr Asn Leu Gly Lys Val Tyr Asp
    290                 295                 300

Tyr Phe Tyr Gln Lys Phe Asn Arg Asn Ser Tyr Asp Asn Lys Gly Gly
305                 310                 315                 320

Lys Ile Val Ser Ser Val His Tyr Gly Ser Arg Tyr Asn Asn Ala Ala
                325                 330                 335

Trp Ile Gly Asp Gln Met Ile Tyr Gly Asp Gly Asp Gly Ser Phe Phe
            340                 345                 350

Ser Pro Leu Ser Gly Ser Met Asp Val Thr Ala His Glu Met Thr His
        355                 360                 365

Gly Val Thr Gln Glu Thr Ala Asn Leu Asn Tyr Glu Asn Gln Pro Gly
    370                 375                 380

Ala Leu Asn Glu Ser Phe Ser Asp Val Phe Gly Tyr Phe Asn Asp Thr
385                 390                 395                 400

Glu Asp Trp Asp Ile Gly Glu Asp Ile Thr Val Ser Gln Pro Ala Leu
                405                 410                 415

Arg Ser Leu Ser Asn Pro Thr Lys Tyr Gly Gln Pro Asp Asn Phe Lys
            420                 425                 430

Asn Tyr Lys Asn Leu Pro Asn Thr Asp Ala Gly Asp Tyr Gly Gly Val
        435                 440                 445

His Thr Asn Ser Gly Ile Pro Asn Lys Ala Ala Tyr Asn Thr Ile Thr
    450                 455                 460

Lys Ile Gly Val Asn Lys Ala Glu Gln Ile Tyr Tyr Arg Ala Leu Thr
465                 470                 475                 480

Val Tyr Leu Thr Pro Ser Ser Thr Phe Lys Asp Ala Lys Ala Ala Leu
                485                 490                 495

Ile Gln Ser Ala Arg Asp Leu Tyr Gly Ser Gln Asp Ala Ala Ser Val
            500                 505                 510

Glu Ala Ala Trp Asn Ala Val Gly Leu
        515                 520

<210> SEQ ID NO 6
```

```
<211> LENGTH: 492
<212> TYPE: PRT
<213> ORGANISM: Bacillus amyloliquefaciens

<400> SEQUENCE: 6

Ser Leu Pro Ile Thr Lys Thr Ser Ala Val Asn Gly Thr Leu Met Gln
1               5                   10                  15

Tyr Phe Glu Trp Tyr Thr Pro Asn Asp Gly Gln His Trp Lys Arg Leu
            20                  25                  30

Gln Asn Asp Ala Glu His Leu Ser Asp Ile Gly Ile Thr Ala Val Trp
        35                  40                  45

Ile Pro Pro Ala Tyr Lys Gly Leu Ser Gln Ser Asp Asn Gly Tyr Gly
50                  55                  60

Pro Tyr Asp Leu Tyr Asp Leu Gly Glu Phe Gln Gln Lys Gly Thr Val
65                  70                  75                  80

Arg Thr Lys Tyr Gly Thr Lys Ser Glu Leu Gln Asp Ala Ile Gly Ser
                85                  90                  95

Leu His Ser Arg Asn Val Gln Val Tyr Gly Asp Val Val Leu Asn His
            100                 105                 110

Lys Ala Gly Ala Asp Ala Thr Glu Asp Val Thr Ala Val Glu Val Asn
        115                 120                 125

Pro Ala Asn Arg Asn Gln Val Thr Ser Glu Glu Tyr Gln Ile Lys Ala
130                 135                 140

Trp Thr Asp Phe Arg Phe Pro Gly Arg Gly Asn Thr Tyr Ser Asp Phe
145                 150                 155                 160

Lys Trp His Trp Tyr His Phe Asp Gly Ala Asp Trp Asp Glu Ser Arg
                165                 170                 175

Lys Ile Ser Arg Ile Phe Lys Phe Arg Gly Glu Gly Lys Ala Trp Asp
            180                 185                 190

Trp Glu Val Ser Ser Glu Asn Gly Asn Tyr Asp Tyr Leu Met Tyr Ala
        195                 200                 205

Asp Val Asp Tyr Asp His Pro Asp Val Val Ala Glu Thr Lys Lys Trp
210                 215                 220

Gly Ile Trp Tyr Ala Asn Glu Leu Ser Leu Asp Gly Phe Arg Ile Asp
225                 230                 235                 240

Ala Ala Lys His Ile Lys Phe Ser Phe Leu Arg Asp Trp Val Gln Ala
                245                 250                 255

Val Arg Gln Ala Thr Gly Lys Glu Met Phe Thr Val Ala Glu Tyr Trp
            260                 265                 270

Gln Asn Asn Ala Gly Lys Leu Glu Asn Tyr Leu Asn Lys Thr Ser Phe
        275                 280                 285

Asn Gln Ser Val Phe Asp Val Pro Leu His Phe Asn Leu Gln Ala Ala
290                 295                 300

Ser Ser Gln Gly Gly Gly Tyr Asp Met Arg Arg Leu Leu Asp Gly Thr
305                 310                 315                 320

Val Val Ser Arg His Pro Glu Lys Ala Val Thr Phe Val Glu Asn His
                325                 330                 335

Asp Thr Gln Pro Gly Gln Ser Leu Glu Ser Thr Val Gln Thr Trp Phe
            340                 345                 350

Lys Pro Leu Ala Tyr Ala Phe Ile Leu Thr Arg Glu Ser Gly Tyr Pro
        355                 360                 365

Gln Val Phe Tyr Gly Asp Met Tyr Gly Thr Lys Gly Thr Ser Pro Lys
370                 375                 380

Glu Ile Pro Ser Leu Lys Asp Asn Ile Glu Pro Ile Leu Lys Ala Arg
```

```
                385                 390                 395                 400
Lys Glu Tyr Ala Tyr Gly Pro Gln His Asp Tyr Ile Asp His Pro Asp
                405                 410                 415

Val Ile Gly Trp Thr Arg Glu Gly Asp Ser Ser Ala Ala Lys Ser Gly
                420                 425                 430

Leu Ala Ala Leu Ile Thr Asp Gly Pro Gly Gly Ser Lys Arg Met Tyr
                435                 440                 445

Ala Gly Leu Lys Asn Ala Gly Glu Thr Trp Tyr Asp Ile Thr Gly Asn
            450                 455                 460

Arg Ser Asp Thr Val Lys Ile Gly Ser Asp Gly Trp Gly Glu Phe His
465                 470                 475                 480

Val Asn Asp Gly Ser Val Ser Ile Tyr Val Gln Lys
                485                 490

<210> SEQ ID NO 7
<211> LENGTH: 4
<212> TYPE: PRT
<213> ORGANISM: Artificial Sequence
<220> FEATURE:
<223> OTHER INFORMATION: synthetic peptide

<400> SEQUENCE: 7

Ala Ala Pro Phe
1
```

FEED COMPOSITION SUPPLEMENTED WITH A PROTEASE COMBINATION

REFERENCE TO A SEQUENCE LISTING

This application contains a Sequence Listing in computer readable form. The computer readable form is incorporated herein by reference.

FIELD OF THE DISCLOSURE

This present application pertains to the field of animal feed supplemented with protease having neutral metalloprotease and serine alkaline protease activity, and use of the protease in an enzyme combination to improve nutritional value of animal diets and animal feed. In particular, the present application relates to an animal feed composition containing a protease combination having neutral metalloprotease and serine protease activity, and amylase.

BACKGROUND OF THE DISCLOSURE

A protease, peptidase or proteinase, is an enzyme that catalyzes or increases the hydrolysis of proteins into smaller polypeptides or single amino acids. Protease, proteinase, or peptidase break the long chainlike molecules of proteins into shorter fragments (peptides) and eventually into amino acid components.

Proteases are involved in body processes including digestion, immune system function, and blood circulation. Proteases are important for the digestion of foods, as well as the digestion of the cell walls of unwanted harmful organisms in the body and break down unwanted wastes such as toxins, cellular debris, and undigested proteins. By breaking down proteins, protease give cells the amino acids needed to function.

Proteases are classified into endopeptidases (target internal peptide bonds) and exopeptidases (target the $NH_2$ and COOH termini). Catalytic classes of proteases in animals include aspartic, metalloproteases, cysteine, serine, and threonine proteases.

Use of proteases in animal feed has been described in the following documents, the disclosures which are incorporated herein in their entirety by reference.

U.S. Pat. No. 6,855,548, the disclosure of which is incorporated herein by reference in its entirety, describes use of acid-stable proteases in animal feed.

U.S. Pat. No. 2,878,123, the disclosure of which is incorporated herein by reference in its entirety, describes use of proteolytic enzymes in poultry feed.

U.S. Pre-Grant Publication No. 20080260894, the disclosure of which is incorporated herein by reference in its entirety, describes use of a multi-protease system to improve the protein digestibility of animal feeds containing vegetable meals.

WO 2005/123911, the disclosure of which is incorporated herein by reference in its entirety, describes polypeptides having protease activity, and use of the polypeptides in animal feed and detergents. WO 2005/123911, the disclosure of which is incorporated herein by reference in its entirety, discloses use of at least one protease: in animal feed; in animal feed additives; in the preparation of a composition for use in animal feed; for improving the nutritional value of an animal feed; for increasing digestible and/or soluble protein in animal feed; for increasing the degree of hydrolysis of proteins in animal diets; and/or for the treatment of proteins. However, WO 2005123911 does not disclose an animal feed composition comprising a specific combination of a metalloprotease, a serine alkaline protease, and amylase, of the present disclosure.

WO 2015/77126, the disclosure of which is incorporated herein by reference in its entirety, discloses an animal feed composition, animal feed additive and/or pet food comprising an amylase and variants thereof. However, WO 2015077126 does not disclose an animal feed composition comprising a specific combination of a metalloprotease, a serine alkaline protease, and amylase, of the present disclosure.

WO 2014/194117, the disclosure of which is incorporated herein by reference in its entirety, describes metalloproteases and compositions containing the metalloprotease for use in cleaning, food, and feed.

In addition, there are a number of commercial protease feed additives on the market (e.g., Commercial Protease A, Commercial protease D). Commercial Protease A is a preparation of serine protease produced by a genetically modified strain of *Bacillus licheniformis*. It is produced by fermentation of a sporulation-deficient *Bacillus licheniformis* strain Rh-3 which expresses a synthetic gene encoding a serine protease (EC 3.4.21.)-derived from *Nocardiopsis prasina* described as a chymotrypsin-type protease. These commercial proteases typically utilize proteases derived from *Bacillus* sp. with a protease composition of primarily serine protease, (as shown in the inhibition assay Table below).

| Samples name | Total Protease (NPU) | Protease activity (incl PMSF) - [Metallo] | Protease activity (Incl. EDTA) [Serine] | MP:SP ratio | % Metallo Protease | % Serine Protease |
|---|---|---|---|---|---|---|
| Com. Prot. A | 63,686 (n = 2) (CV = 6%) | 0 (n = 2) | 58,555 (n = 1) | n/a | 8 | 100 |
| Com. Prot D | 11,762 (n = 1) | 0 (n = 2) | 11,694 (n = 1) | n/a | 1 | 100 |

For instance, Commercial protease D is a feed additive in which the protease is derived from *Bacillus licheniformis*, and displays Keratinolytic activity. Commercial Protease A is a feed additive in which serine protease is derived from *Nocardiopsis prasina* that is genetically modified, and displays Keratinolytic activity, with optimum activities under alkaline conditions.

An additional commercial protease product is Commercial protease D). This is a commercial preparation of serine protease (EC 3.4.21.19) produced by *Bacillus Licheniformis*.

SUMMARY OF THE DISCLOSURE

The present invention relates to a protease combination or a protease mixture having neutral metalloprotease and serine alkaline protease activity, for use to improve digestibility of proteins, and in particular, digestibility of animal feed, and to optimize the nutritional value of an animal diet or animal feed.

In one embodiment, the protease combination or protease mixture is further combined with an amylase.

The disclosure also relates to isolated polypeptides having neutral metalloprotease and serine alkaline protease activity, and isolated nucleic acid sequences encoding such polypeptides.

In one embodiment, the invention relates to an isolated serine alkaline protease polypeptide, and an isolated nucleic acid sequence encoding the same, as well as an isolated neutral metalloprotease and an isolated nucleic acid sequence encoding the same. The serine alkaline protease [AprE] and neutral metalloprotease [NprE] sequences are derived from the genome of *Bacillus* sp., preferably, *Bacillus amyloliquefaciens*.

A serine alkaline protease or homolog thereof, selected from the group consisting of: (i) a serine alkaline protease comprising or consisting of the polypeptide of SEQ ID NO: 1, or a fragment thereof; (ii) a serine alkaline protease comprising or consisting of an amino acid sequence having at least 99%, at least 98%, at least 97%, at least 96%, at least 95%, at least 90%, at least 85%, or at least 80% identity to the polypeptide of SEQ ID NO: 1, and (iii) a serine alkaline protease encoded by a polynucleotide comprising or consisting of a nucleotide sequence having at least 99%, at least 98%, at least 97%, at least 96%, at least 95%, at least 90%, at least 85%, or at least 80% sequence identity to the polypeptide coding sequence of SEQ ID NO: 1.

A serine alkaline protease or homolog thereof, selected from the group consisting of: (i) a serine alkaline protease comprising or consisting of the polypeptide of SEQ ID NO: 4 or a fragment thereof; (ii) a serine alkaline protease comprising or consisting of an amino acid sequence having at least 99%, at least 98%, at least 97%, at least 96%, at least 95%, at least 90%, at least 85%, or at least 80% identity to the polypeptide of SEQ ID NO: 4, and (iii) a serine alkaline protease encoded by a polynucleotide comprising or consisting of a nucleotide sequence having at least 99%, at least 98%, at least 97%, at least 96%, at least 95%, at least 90%, at least 85%, or at least 80% sequence identity to the polypeptide coding sequence of SEQ ID NO: 4.

A metalloprotease or homolog thereof, selected from the group consisting of: (i) a metalloprotease comprising or consisting of the polypeptide of SEQ ID NO: 2, or a fragment thereof; (ii) a metalloprotease comprising or consisting of an amino acid sequence having at least 99%, at least 98%, at least 97%, at least 96%, at least 95%, at least 90%, at least 85%, or at least 80% identity to the polypeptide of SEQ ID NO: 2, and (iii) a metalloprotease encoded by a polynucleotide comprising or consisting of a nucleotide sequence having at least 99%, at least 98%, at least 97%, at least 96%, at least 95%, at least 90%, at least 85%, or at least 80% sequence identity to the polypeptide coding sequence of SEQ ID NO: 2.

A metalloprotease or homolog thereof, selected from the group consisting of: (i) a metalloprotease comprising or consisting of the polypeptide of SEQ ID NO: 5, or a fragment thereof; (ii) a metalloprotease comprising or consisting of an amino acid sequence having at least 99%, at least 98%, at least 97%, at least 96%, at least 95%, at least 90%, at least 85%, or at least 80% identity to the polypeptide of SEQ ID NO: 5, and (iii) a metalloprotease encoded by a polynucleotide comprising or consisting of a nucleotide sequence having at least 99%, at least 98%, at least 97%, at least 96%, at least 95%, at least 90%, at least 85%, or at least 80% sequence identity to the polypeptide coding sequence of SEQ ID NO: 5.

In another embodiment, the invention relates to an isolated α-amylase polypeptide, and an isolated nucleic acid sequence encoding the same. The α-amylase is derived from the genome of *Bacillus* sp., preferably, *Bacillus amyloliquefaciens*.

An α-amylase or homolog thereof, selected from the group consisting of: (i) an α-amylase comprising or consisting of the polypeptide of SEQ ID NO: 3, or a fragment thereof; (ii) an α-amylase comprising or consisting of an amino acid sequence having at least 99%, at least 98%, at least 97%, at least 96%, at least 95%, at least 90%, at least 85%, or at least 80% identity to the polypeptide of SEQ ID NO: 3, and (iii) an α-amylase encoded by a polynucleotide comprising or consisting of a nucleotide sequence having at least 99%, at least 98%, at least 97%, at least 96%, at least 95%, at least 90%, at least 85%, or at least 80% sequence identity to the polypeptide coding sequence of SEQ ID NO: 3.

An α-amylase or homolog thereof, selected from the group consisting of: (i) an α-amylase comprising or consisting of the polypeptide of SEQ ID NO: 6, or a fragment thereof; (ii) an α-amylase comprising or consisting of an amino acid sequence having at least 99%, at least 98%, at least 97%, at least 96%, at least 95%, at least 90%, at least 85%, or at least 80% identity to the polypeptide of SEQ ID NO: 6, and (iii) an α-amylase encoded by a polynucleotide comprising or consisting of a nucleotide sequence having at least 99%, at least 98%, at least 97%, at least 96%, at least 95%, at least 90%, at least 85%, or at least 80% sequence identity to the polypeptide coding sequence of SEQ ID NO: 6.

According to one embodiment of the present disclosure, a method for improving digestibility of proteins is provided which, involves administering to an animal, a protease combination or a protease mixture having neutral metalloprotease and serine alkaline protease activity. In a particular embodiment, the method for improving digestibility of proteins involves administering the protease combination or the protease mixture with α-amylase.

The animal may include, but is not limited to, amphibians, fish, reptiles, birds, or mammals. In a preferred embodiment, the animal is a mammalian or non-mammal monogastric, including, but not limited to, humans, primates, poultry, swine, dogs, cats, or horses.

In another embodiment of the present disclosure, a method of improving digestibility of animal feed is provided which, involves adding to the animal feed, a protease combination or a protease mixture having neutral metalloprotease and serine alkaline protease activity.

In yet another embodiment of the present disclosure, a method of optimizing nutritional value of an animal feed is provided which, involves adding to the animal feed, a protease combination or a protease mixture having neutral metalloprotease and serine alkaline protease activity.

The animal feed of the present methods is provided to an animal including, but not limited to, amphibians, fish, reptiles, birds or mammals. In a preferred embodiment, the animal is preferably, a mammalian or non-mammal monogastric including, but not limited to, humans, primates, poultry, swine, dogs, cats, or horses.

The protease combination in the methods of the present disclosure has a ratio of total activity of neutral metalloprotease:serine alkaline protease of from 4:1 to 1.5:1.

Preferably, the protease combination or the protease mixture in the methods of the present disclosure, is in a feed additive or feed supplement. The feed additive may be powder that is added pre-pelleting, or a liquid that is applied (e.g., sprayed) post-pelleting.

In a preferred embodiment, the methods of the present disclosure involves a mixture of amylase with the protease combination or protease mixture. The amylase may be one or more of an α-amylase, a β-amylase, or a γ-amylase.

In another preferred embodiment, when the methods of the present disclosure includes the protease combination or the protease mixture, and the amylase, the protease combination or the protease mixture and the amylase has a ratio of total activity of protease:amylase of from 20:1.13 to 1:5; more preferably, the protease combination or the protease mixture and the amylase has a ratio of total activity of protease:amylase of from 20:1.13 to 1:1.36. Preferably, the ratio of total activity of protease:amylase is 9:1.13, more preferably, the ratio of total activity of protease:amylase is 1:1.4. Most preferably, the ratio of total activity of protease:amylase is 1:1.36.

In another preferred embodiment, the protease combination or the protease mixture in the methods of the present disclosure is derived from *Bacillus* sp. and preferably, from *Bacillus amyloliquefaciens*.

In another aspect of the present disclosure, a feed additive is provided containing a protease combination or a protease mixture having neutral metalloprotease and a serine alkaline protease activity. The neutral metalloprotease and serine alkaline protease have a ratio of total activity of neutral metalloprotease:alkaline serine protease of from 4:1 to 1.5:1.

In a preferred embodiment of this aspect of the disclosure, the feed additive further includes an amylase. The amylase may be one or more of an α-amylase, a β-amylase, and a γ-amylase.

In another preferred embodiment of this aspect of the disclosure, when the feed additive includes the protease combination or the protease mixture and the amylase, the protease combination or the protease mixture and the amylase has a ratio of total activity of protease:amylase of from 20:1.13 to 1:5. Preferably, the ratio of total activity of protease:amylase is 9:1.13, and more preferably, the ratio of total activity of protease:amylase is 1:1.4. Most preferably, the ratio of total activity of protease:amylase is 1:1.36.

In another preferred embodiment of this aspect of the disclosure, the protease combination or the protease mixture in the feed additive of the present disclosure is derived from *Bacillus* sp. and preferably, from *Bacillus amyloliquefaciens*.

In further aspect of the present disclosure, an enzyme composition is provided containing a protease combination or a protease mixture having neutral metalloprotease and a serine alkaline protease activity. The neutral metalloprotease and serine alkaline protease have a ratio of total activity of neutral metalloprotease:alkaline serine protease of from 4:1 to 1.5:1.

In a preferred embodiment of this aspect of the disclosure, the enzyme composition further includes an amylase. The amylase may be one or more of an α-amylase, a β-amylase, and a γ-amylase.

In another preferred embodiment of this aspect of the disclosure, when the enzyme composition includes the protease combination or the protease mixture and the amylase, the protease combination or the protease mixture and the amylase has a ratio of total activity of protease:amylase of from 20:1.13 to 1:2. Preferably, the ratio of total activity of protease:amylase is 9:1.13, and more preferably, the ratio of total activity of protease:amylase is 1:1.4. Most preferably, the ratio of total activity of protease:amylase is 1:1.36.

In a preferred embodiment of this aspect of the disclosure, the enzyme composition is in a feed formulation.

In another preferred embodiment of this aspect of the disclosure, the protease combination or the protease mixture in the enzyme composition of the present disclosure is derived from *Bacillus* sp. and preferably, from *Bacillus amyloliquefaciens*.

In another aspect of the disclosure, the present disclosure provides for a kit for improving the nutritional value of an animal diet or animal feed. The kit includes (a) an enzyme combination that contains a protease combination or a protease mixture having neutral metalloprotease and serine alkaline protease activity, and an amylase, and (b) instructions to enable supplementation of the animal diet or the animal feed with the enzyme combination. The protease combination or the protease mixture in the kit has a ratio of total activity of neutral metalloprotease:alkaline serine protease of from 4:1 to 1.5:1, and the protease combination or the protease mixture and amylase have a ratio of total activity of protease:amylase of from 20:1.13 to 1:5. Preferably, the ratio of total activity of protease:amylase is 9:1.13, and more preferably, the ratio of total activity of protease:amylase is 1:1.4. Most preferably, the ratio of total activity of protease:amylase is 1:1.36.

In a preferred embodiment of this aspect of the disclosure, the amylase in the kit may be one or more of an α-amylase, a β-amylase, and a γ-amylase.

In a preferred embodiment of this aspect of the disclosure, the ratio of total activity of protease:amylase in the kit is 9:1.13, and more preferably, the ratio of total activity of protease:amylase is 1:1.4. Most preferably, the ratio of total activity of protease:amylase is 1:1.36.

In a preferred embodiment of this aspect of the disclosure, the protease combination or the protease mixture in the kit is derived from *Bacillus* sp. and preferably, from *Bacillus amyloliquefaciens*.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE DISCLOSURE

Figure 1:
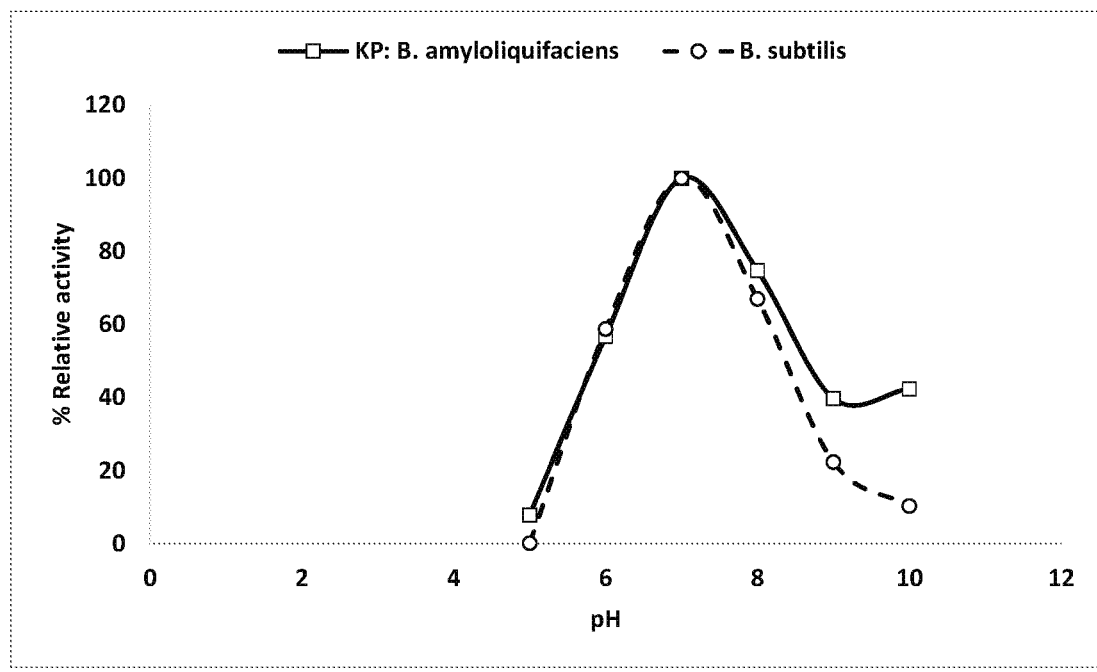
FIG. 1 depicts relative protease activity in response to pH.

The details of embodiments of the presently disclosed subject matter are set forth in the accompanying description below. Other features, objects, and advantages of the presently disclosed subject matter will be apparent from the specification, figures, and claims. All publications, patent applications, patents, and other references noted herein are incorporated by reference in their entirety.

The term "isolated" means a substance in a form or environment that does not occur in nature. Examples of isolated substances include, but are not limited to, (1) any non-naturally occurring substance, (2) any substance including, but not limited to, any enzyme, variant, nucleic acid, protein, or peptide, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

The term "fragment" means a polypeptide having one or more (e.g., several) amino acids absent from the mature polypeptide. In one aspect, a fragment contains at least at least 50%, at least 55%, at least 60%, at least 65%, at least 70%, at least 75%, at least 80%, at least 85%, at least 90%, at least 95%, but less than 100% of the amino acid residues of the mature polypeptide of an enzyme. For instance, 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, of the amino acid residues of the mature polypeptide of an enzyme.

The terms "comprise," "comprises," "comprising," "include," "includes," and "including" are interchangeable and not intended to be limiting. It is to be further understood that where descriptions of various embodiments use the term "comprising," those skilled in the art would understand that the present disclosure also contemplates such embodiments alternatively described using the language "consisting essentially of" or "consisting of."

The technical field of this disclosure is biotechnology and the exogenous supplementation of enzymes to animal feed (or animal nutrition). Enzymes are widely used in feed to improve nutrient utilization. Proteases are commonly used as feed additives with the purpose of increasing dietary protein hydrolysis and facilitating an improved nitrogen utilization for basal metabolism and growth of the monogastric animal.

This application relates to use of a protease combination or a protease mixture having neutral metalloprotease and serine alkaline protease activity, which is obtained by a specific fermentation process. The protease combination or the protease mixture has the neutral metalloprotease and serine alkaline protease in a specific ratio as described herein, and is useful as a feed additive to improve amino acid digestibility in monogastric feeds. The protease combination or the protease mixture may be further combined with an amylase enzyme in a specific ratio(s) of total protease(s)/amylase(s).

This disclosure describes the effects of a novel protease enzyme having neutral metalloprotease and serine alkaline protease activity in an enzyme combination that includes amylase, in which the protease and amylase have specific ratios of total activity of protease(s)/amylases.

The protease combination of the present disclosure may be a metalloprotease and a serine alkaline protease as described in the Handbook of Proteolytic Enzymes, 3$^{rd}$ Edition, A. Barrett, N. D. Rawlings, J. Woessner (eds.), Academic Press (2012), the Chapters on Metallopeptidases: Introduction: metallopeptidases and their clans and Serine Peptidases, the disclosure of which is incorporated herein in its entirety by reference.

The present disclosure also relates to isolated polypeptides having neutral metalloprotease and serine alkaline protease activity, and the corresponding isolated nucleic acid sequences. The isolated polypeptides may comprise an amino acid sequence having a certain degree of identity to a specified amino acid sequence with a specified SEQ ID NO, or specified fragments thereof corresponding to the mature polypeptides. Similarly, isolated nucleic acids of the present disclosure may comprise a nucleic acid sequence having a certain degree of identity to a specified a nucleic acid sequence with a specified SEQ ID NO: or specified fragment encoding parts thereof of the mature polypeptide.

The serine alkaline protease [AprE], neutral metalloprotease [NprE], and alpha-amylase sequences were derived from the genome of *Bacillus* sp. and preferably, from *Bacillus amyloliquefaciens*. These sequences were used as query sequences to BLAST (blastp) against the predicted proteome protease of the present disclosure. Amino acid sequences with the highest degree of homology to the query sequences were identified. These sequences were further aligned to the query sequence to assess query coverage. A consensus sequence for AprE, NprE and α-amylase was formed from the alignments. Synthetic conservation of the consensus sequence was compared to orthologues of other closely-related *Bacillus* spp. to further evaluate the completeness of the consensus sequences.

A protein engineered variant of an enzyme (or protein) of the present disclosure may also be used, as well as a polynucleotide encoding the variant of the enzyme (or protein).

The present invention also relates to isolated polynucleotides encoding the variants; nucleic acid constructs, vectors, and host cells comprising the polynucleotides; and methods of producing the polypeptide or variant thereof, and use of the polypeptide or variant thereof.

In an embodiment, the variant has sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the polypeptide sequence of an enzyme in the present disclosure, or is a fragment of the polypeptide sequence of an enzyme in the present disclosure. In addition, the invention relates to a polynucleotide encoding the polypeptide sequence of such a variant enzyme or a subsequence encoding a fragment of the polypeptide sequence of an enzyme of the present disclosure.

In one aspect, the variant is an serine alkaline protease variant, and/or a polynucleotide encoding the serine alkaline protease variant. The serine alkaline protease variant comprises a substitution, insertion, and/or deletion at one or more (several) amino acid position(s) of SEQ ID NO: 1 or a fragment of SEQ ID NO: 1, wherein the variant has serine alkaline protease activity. In an embodiment, the serine alkaline protease variant has sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the polypeptide of SEQ ID NO: 1.

Alternatively, the serine alkaline protease variant comprises a substitution, insertion, and/or deletion at one or more (several) amino acid position(s) of SEQ ID NO: 4 or a fragment of SEQ ID NO: 4, wherein the variant has serine alkaline protease activity. In an embodiment, the serine alkaline protease variant has sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the polypeptide of SEQ ID NO: 4.

In another aspect, the variant is a metalloprotease variant, and/or a polynucleotide encoding the metalloprotease variant. The metalloprotease variant comprises a substitution, insertion, and/or deletion at one or more (several) amino acid position(s) of SEQ ID NO: 2 or a fragment of SEQ ID NO: 2, wherein the variant has metalloprotease activity. In an embodiment, the metalloprotease variant has sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the polypeptide of SEQ ID NO: 2.

Alternatively, the metalloprotease variant comprises a substitution, insertion, and/or deletion at one or more (several) amino acid position(s) of SEQ ID NO: 5 or a fragment of SEQ ID NO: 5, wherein the variant has metalloprotease activity. In an embodiment, the metalloprotease variant has sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the polypeptide of SEQ ID NO: 5.

In yet another aspect, the variant is an α-amylase variant and/or a polynucleotide encoding the α-amylase variant. The α-amylase variant comprises a substitution, insertion, and/or deletion at one or more (several) amino acid position(s) of SEQ ID NO: 3 or a fragment of SEQ ID NO: 3, wherein the variant has α-amylase activity. In an embodiment, the α-amylase variant has sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the polypeptide of SEQ ID NO: 3.

Alternatively, the α-amylase variant comprises a substitution, insertion, and/or deletion at one or more (several) amino acid position(s) of SEQ ID NO: 6 or a fragment of SEQ ID NO: 6, wherein the variant has α-amylase activity. In an embodiment, the α-amylase variant has sequence identity of at least 80%, e.g., at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, but less than 100%, to the polypeptide of SEQ ID NO: 6.

A serine alkaline protease or homolog thereof, selected from the group consisting of: (i) a serine alkaline protease comprising or consisting of the polypeptide of SEQ ID NO: 1; (ii) a serine alkaline protease comprising or consisting of an amino acid sequence having at least 99%, at least 98%, at least 97%, at least 96%, at least 95%, at least 90%, at least 85%, or at least 80%, but less than 100%, identity to the polypeptide of SEQ ID NO: 1, (iii) a serine alkaline protease encoded by a polynucleotide comprising or consisting of a nucleotide sequence having at least 99%, at least 98%, at least 97%, at least 96%, at least 95%, at least 90%, at least 85%, or at least 80%, but less than 100%, sequence identity to the polypeptide coding sequence of SEQ ID NO: 1, and (iv) a serine protease encoded by a polynucleotide that hybridizes under low stringency conditions or high stringency conditions with the polypeptide coding sequence of SEQ ID NO: 1.

A serine alkaline protease or homolog thereof, selected from the group consisting of: (i) a serine alkaline protease comprising or consisting of the polypeptide of SEQ ID NO: 4; (ii) a serine alkaline protease comprising or consisting of an amino acid sequence having at least 99%, at least 98%, at least 97%, at least 96%, at least 95%, at least 90%, at least 85%, or at least 80%, but less than 100%, identity to the polypeptide of SEQ ID NO: 4, (iii) a serine alkaline protease encoded by a polynucleotide comprising or consisting of a nucleotide sequence having at least 99%, at least 98%, at least 97%, at least 96%, at least 95%, at least 90%, at least 85%, or at least 80%, but less than 100%, sequence identity to the polypeptide coding sequence of SEQ ID NO: 4, and (iv) a serine protease encoded by a polynucleotide that hybridizes under low stringency conditions or high stringency conditions with the polypeptide coding sequence of SEQ ID NO: 4.

A metalloprotease or homolog thereof, selected from the group consisting of: (i) a metalloprotease comprising or consisting of the polypeptide of SEQ ID NO: 2; (ii) a metalloprotease comprising or consisting of an amino acid sequence having at least 99%, at least 98%, at least 97%, at least 96%, at least 95%, at least 90%, at least 85%, or at least 80%, but less than 100%, identity to the polypeptide of SEQ ID NO: 2, (iii) a metalloprotease encoded by a polynucleotide comprising or consisting of a nucleotide sequence having at least 99%, at least 98%, at least 97%, at least 96%, at least 95%, at least 90%, at least 85%, or at least 80%, but less than 100%, sequence identity to the polypeptide coding sequence of SEQ ID NO: 2, and (iv) a metalloprotease encoded by a polynucleotide that hybridizes under low stringency conditions or high stringency conditions with the polypeptide coding sequence of SEQ ID NO: 2.

A metalloprotease or homolog thereof, selected from the group consisting of: (i) a metalloprotease comprising or consisting of the polypeptide of SEQ ID NO: 5; (ii) a metalloprotease comprising or consisting of an amino acid sequence having at least 99%, at least 98%, at least 97%, at least 96%, at least 95%, at least 90%, at least 85%, or at least 80%, but less than 100%, identity to the polypeptide of SEQ ID NO: 5, (iii) a metalloprotease encoded by a polynucleotide comprising or consisting of a nucleotide sequence having at least 99%, at least 98%, at least 97%, at least 96%, at least 95%, at least 90%, at least 85%, or at least 80%, but less than 100%, sequence identity to the polypeptide coding sequence of SEQ ID NO: 5, and (iv) a metalloprotease encoded by a polynucleotide that hybridizes under low stringency conditions or high stringency conditions with the polypeptide coding sequence of SEQ ID NO: 5.

An α-amylase or homolog thereof, selected from the group consisting of: (i) an α-amylase comprising or consisting of the polypeptide of SEQ ID NO: 3; (ii) an α-amylase comprising or consisting of an amino acid sequence having at least 99%, at least 98%, at least 97%, at least 96%, at least 95%, at least 90%, at least 85%, or at least 80%, but less than 100%, identity to the polypeptide of SEQ ID NO: 3, (iii) an α-amylase encoded by a polynucleotide comprising or consisting of a nucleotide sequence having at least 99%, at least 98%, at least 97%, at least 96%, at least 95%, at least 90%, at least 85%, or at least 80%, but less than 100%, sequence identity to the polypeptide coding sequence of SEQ ID NO: 3, and (iv) an α-amylase encoded by a polynucleotide that hybridizes under low stringency conditions or high stringency conditions with the polypeptide coding sequence of SEQ ID NO: 3.

An α-amylase or homolog thereof, selected from the group consisting of: (i) an α-amylase comprising or consisting of the polypeptide of SEQ ID NO: 6; (ii) an α-amylase comprising or consisting of an amino acid sequence having at least 99%, at least 98%, at least 97%, at least 96%, at least 95%, at least 90%, at least 85%, or at least 80%, but less than 100%, identity to the polypeptide of SEQ ID NO: 6, (iii) an α-amylase encoded by a polynucleotide comprising or consisting of a nucleotide sequence having at least 99%, at least 98%, at least 97%, at least 96%, at least 95%, at least 90%, at least 85%, or at least 80%, but less than 100%, sequence identity to the polypeptide coding sequence of SEQ ID NO: 6, and (iv) an α-amylase encoded by a polynucleotide that hybridizes under low stringency conditions or high stringency conditions with the polypeptide coding sequence of SEQ ID NO: 6.

Hybridization indicates that the polynucleotide hybridizes to a labeled nucleic acid probe corresponding to (i) the polypeptide coding sequence of SEQ ID NO: 1, 2, 3, 4, 5, or 6 or variant thereof; (ii) the cDNA sequence thereof; (iii) the full-length complement thereof; or (iv) a subsequence thereof; under high or low stringency conditions. Hybridization may occur under high stringency conditions as described above. Alternatively, hybridization may occur under low stringency conditions.

High stringency conditions are defined as prehybridization and hybridization at 42° C. in 5×SSPE, 0.3% SDS, 200 µg/ml sheared and denatured salmon sperm DNA, 35% formamide to 50% formamide, following standard Southern blotting procedures for 12 to 24 hours optimally. The carrier material is washed three times each for 15 minutes using 2×SSC, 0.2% SDS preferably at 55° C. to 70° C.

Low stringency conditions are defined as prehybridization and hybridization at 42° C. in 5×SSPE, 0.3% SDS, 200 µg/ml sheared and denatured salmon sperm DNA, 25% formamide to below 35% formamide, following standard Southern blotting procedures for 12 to 24 hours optimally. The carrier material is washed three times each for 15 minutes using 2×SSC, 0.2% SDS preferably at 45° C. to below 55° C.

The proteases or protease variants as described herein may be used as a protease combination or protease mixture, or preferably, used with an amylase or amylase variant in the combinations, uses, compositions and methods of the disclosure as set out herein and in the claims.

There origins of the metalloprotease or the serine alkaline protease are not limited. The metalloprotease or serine alkaline protease may be a natural or wild-type protease obtained from microorganisms of any genus, isolated proteases, genetically engineered proteases, recombinant proteases, or synthetic proteases. Genetically engineered metalloprotease or serine alkaline protease may be prepared based on well-known methods in in the art, including, but not limited to, site-specific mutagenesis, chimeragenesis, PCR, random mutagenesis, or recombination.

Standard procedures for cloning of genes and introducing mutations (random and/or site directed) may be used in order to obtain enzymes and enzyme variants such as the protease variants of the disclosure. For instance, techniques used to isolate or clone a polynucleotide are known in the art and include isolation from genomic DNA or cDNA, or a combination thereof. The cloning of the polynucleotides from genomic DNA can be effected, e.g., by using polymerase chain reaction (PCR) or antibody screening of expression libraries to detect cloned DNA fragments with shared structural features. See, e.g., Innis et al., 1990, PCR: A Guide to Methods and Application, Academic Press, New York. Other nucleic acid amplification procedures such as ligase chain reaction (LCR), ligation activated transcription (LAT) and polynucleotide-based amplification (NASBA) may be used. Additional exemplary techniques are as described in Sambrook et al. (2012), Molecular cloning: A laboratory manual, Cold Spring Harbor lab., Cold Spring Harbor, N.Y.; Ausubel, F. M. et al. (eds.) "Current protocols in Molecular Biology". John Wiley and Sons, 2003; Harwood, C. R., and Cutting, S. M. (eds.) "Molecular Biological Methods for *Bacillus*". John Wiley and Sons, 1990.

Preferably, the protease enzyme combination or the protease enzyme mixture is obtained by a specific fermentation process from a singlestrain of *Bacillus*, preferably a non-genetically modified strain of *Bacillus*, preferably, *Bacillus amyloliquefaciens*. In such case, a protease enzyme cocktail is produced through a fermentation process using *B. amyloliquefaciens*. The bacteria are fermented for 24 hours at 30° C. in the presence of maltodextrin and a complex nitrogen source (soy flour), in order to produce the enzyme cocktail. Following fermentation, this product goes through a number of steps including microfiltration, diafiltration and ultrafiltration, to remove solids and concentrate the liquid enzyme preparation. Following these steps, the product is spray dried to a carrier and provided a granulated powder product or stabilized as a liquid. In the case of the stabilized liquid the product will not go through the drying phase.

Protease activity can be measured using any assay, in which a substrate that includes peptide bonds relevant for the specificity of the metalloprotease and serine alkaline protease is used, as exemplified herein in the Examples. Examples of assay-pH-values include pH 2, 3, 4, 5, 6, 7, 8, 9, 10, 11, or 12, and examples of assay-temperatures are 30° C., 35° C., 37° C., 40° C., 45° C., 50° C., 55° C., 60° C., 65° C., 70° C., 80° C., 90° C., or 95° C. Preferably, the assay used to determine the ratio of total activity of neutral metalloprotease:alkaline serine protease is the NPU assay method.

The protease combination or the protease mixture may be used in an additive composition/formulation or animal feed additive.

A formulation or feed additive containing the protease combination or the protease mixture of the present disclosure may be added to animal feed in either a powder form or a liquid form. the feed additive may be powder that is added pre-pelleting, or a liquid that is applied (e.g., sprayed) post-pelleting.

For example, when in a powdered form, the composition of the feed additive is a low dust, dry blended and/or microgranulated enzyme powder derived from the natural fermentation of *B. amyloliquefaciens* (see fermentation described herein) combined with a suitable carrier agent, including but not limited to, rice bran, cereal, pseudocereal, wheat flour and/or calcium sulphate dihydrate (Gypsum—$CaSO_4$), which is used to assist with mixing of the product in feed (see feed mixing and palletization process conditions described below). This product is made from a natural raw material and as such may be subject to some batch to batch colour and/or odour variation, but these variations are not an indicator of enzyme activity and do not impact on product performance. The enzyme combination product maintains a combination of a neutral metalloprotease, serine alkaline protease and amylase activities in a specific ratio. The enzyme combination of the present disclosure provides the protease combination or the protease mixture having metalloprotease activity and serine alkaline protease activity in a certain ratio with any type of amylase, including but not limited to, fungal amylase, bacterial amylase, α-amylase, and 3-amylase. The protease enzyme formulation/additive comprises of 80-55% Metalloprotease [% of the total protease activity—as per the analytical method described herein below], and 20-45% serine protease [% of the total protease activity as per the analytical method described herein below].

The enzymes in the present disclosure may be encapsulated to improve thermal protection. Examples of such encapsulation techniques include, but are not limited to, liposomal vesicles, hydrogel (such as poly(ethylene glycol) (PEG) hydrogel spheres, polymers (such as micellar polymer encapsulation like chitosan and Nafion), sol-gel, polyelectrolytes, and nanotubes of peptides and lipid.

The enzyme (protease) formulation or feed additive containing the protease combination or the protease mixture of the present disclosure maintains a protease:amylase ratio of 20:1.13 to 1:5, preferably, 9:1.13, and more preferably, 1:1.4. Most preferably, the ratio of total activity of protease:amylase is 1:1.36. See Table 1.3.

In liquid form, the composition of the feed additive is a stabilized enzyme liquid derived from the natural fermentation of *B. amyloliquefaciens* (see fermentation process described herein). Enzyme stabilization is achieved through the combination of glycerol as a stabilizer and preservatives such as calcium chloride and potassium sorbate which are added at the end of fermentation. This product is made from a natural raw material and as such may be subject to some batch to batch colour and/or odour variation, but these variations are not an indicator of enzyme activity and do not impact on product performance. The enzyme combination product maintains combination of a neutral metalloprotease, serine alkaline protease and amylase activities in a specific ratio. The enzyme combination of the present disclosure provides the protease combination or the protease mixture having metalloprotease activity and serine alkaline protease activity in a certain ratio with any type of amylase, including but not limited to, fungal amylase, bacterial amylase, α-amylase, and β-amylase. The protease enzyme formulation/additive comprises of 80-55% Metalloprotease [% of the total protease activity—as per the analytical method described herein below], and 20-45% serine protease [% of the total protease activity as per the analytical method described herein below]. The amylase activity described in this disclosure is a bacterial amylase containing α-amylase, β-amylase activities. The enzyme (protease) formulation or feed additive containing the protease combination or the protease mixture of the present disclosure maintains a protease:amylase ratio of 20:1.13 to 1:5, preferably, 9:1.13, and more preferably, 1:1.4. Most preferably, the ratio of total activity of protease:amylase is 1:1.36. See Table 1.3.

An animal feed or additive composition of the present disclosure may be used in feed for an animal including, but not limited to, amphibians, aquaculture species (like fish), reptiles, birds, or mammals. Preferably, the animal is a fish or a mammal. The mammal is preferably, a monogastric species including, but not limited to, humans, primates, poultry, swine, companion animals (like dogs and cats), or horses. An animal feed or additive composition of the present disclosure may also be used in feed of ruminants.

The animal feed composition typically contains 0-80% maize, and/or 0-80% sorghum; and/or 0-70% wheat; and/or 0-70% barley; and/or 0-30% oats; and/or 0-40% soybean meal; and/or 0-25% fish meal; and/or 0-25% meat and bone meal; and/or 0-20% whey.

Animal diets can be manufactured as mash feed (non-pelleted) or pelleted feed (as whole pellets or crumbs). Typically, the milled feed-stuffs are mixed and sufficient amounts of essential vitamins and mineral are added according to the specifications for the species in question. The protease enzyme combination (protease combination) or protease enzyme mixture (protease mixture) of the present disclosure may be added to the feed (as solid or liquid), or to a given as a feed additive or premix. The enzyme concentration in the diet is typically within the range of 0.01-500 g enzyme protein per MT diet.

The protease enzyme combination or the protease enzyme mixture, when used as a feed additive for monogastric feed, functions in protein solubilization and hydrolysis, with a concomitant improvement in digestibility which has subsequent effects/impact on growth performance in monogastric animals.

The aim of this disclosure is the use of a protease combination or a protease mixture consisting essentially of neutral metalloprotease and serine alkaline protease in a described ratio. The protease combination or the protease mixture may further be combined with an amylase in specific total protease(s)/amylases ratio(s). The protease combination or the protease mixture is obtained by a specific fermentation process as a feed additive to improve amino acid digestibility in the feed of monogastric animals.

The present disclosure involves a protease enzyme combination or a protease enzyme mixture capable of hydrolyzing storage proteins and anti-nutrients in vegetarian feed formulations as well as those of animal derived proteins for monogastric animals, delivering improved amino acid digestibility.

When used as a feed or dietary additive or supplement, the protease combination or the protease mixture described herein achieves the following unexpected improvements:

Facilitates the utilization of feed-derived protein, peptides and amino acids by a mammalian or non-mammalian monogastric for supporting its basal metabolism and growth (Table 1.1-1.2).

Enable the nutritional optimization of monogastric feed formulations as a result of the increased digestibility of the protein fraction of the diet (Table 1.1-1.2).

Provide improved body weight and feed conversion ratio of monogastric animals fed a protein deficient (i.e., crude protein and amino acids) feed formulation compared to a group of animals on the same non-protease supplemented diet (Table 1.1-1.2).

Increase the sustainability of monogastric animal production by maximizing nutrient utilization and therefore reducing the excretion of undigested proteins (Table 1.1-1.2).

The present disclosure provides a protease combination or mixture having both metalloprotease and serine protease activity, produced preferably, from a *Bacillus amyloliquefaciens* strain to deliver improved performance for protein hydrolysis, especially when used in combination with an amylase. The present disclosure is of high commercial significance and provides an enzyme formulation which can be used as a feed additive in monogastric nutrition.

The present disclosure allows for a reduction in the digestible protein and/or digestible amino acids included in feed formulations. This reduction is then compensated by the efficacy of the protease combination or mixture, which acts to increase the digestibility of the reduced protein diet.

The protease enzyme combination or protease enzyme mixture may be included in a protease enzyme formulation/feed additive in which the protease enzyme combination or the protease enzyme mixture is one consisting essentially of a neutral metalloprotease accounting for 80-55% of the total activity and an alkaline serine protease accounting for 20-45% of the total activity, or a ratio of total activity of neutral metalloprotease:alkaline serine protease of from 4:1 to 1.5:1. Alternatively, the protease enzyme combination or the protease enzyme mixture is one consisting essentially of a neutral metalloprotease accounting for 80-60% of the total activity and an alkaline serine protease accounting for 25-45% of the total activity, or a ratio of total activity of neutral metalloprotease:alkaline serine protease may be from 3:1 to 1.5:1.

In another embodiment, the weights of each of the neutral metalloprotease, alkaline serine protease and amylase components present in the enzyme formulations, feed additives, and compositions of the present disclosure, may be based on total active protein. In such case, the percentage ratios are calculated based on the total composition unless otherwise indicated.

Amylases useful in the present disclosure may include α-Amylases, β-Amylases, or γ-Amylases. α-Amylases useful in the present disclosure include, but are not limited to, endo-hydrolase (which act on the interior of the substrate molecule) and exo-hydrolase (which act on the terminal non reducing ends) and may be variant amylases as described in WO 2015/077126, the disclosure of which is herein incorporated in its entirety by reference.

The neutral metalloprotease, alkaline serine protease and amylase may be isolated from plants, animals or microorganisms. Preferably, the neutral metalloprotease, alkaline serine protease and amylase components may each be obtained from microbial sources such as, bacteria, fungi and genetically modified species of microbes.

Bacterial sources include, but are not limited to, the *Bacillus* sp. (such as *B. amyloliquefaciens, B. velezensis, B. licheniformis, B. pumilus, B. safensis, B. altitudinis, B. aerophilus, B. subtilis, B. carboniphilus, B. sporothermodorans, B. stearothermophilus, B. dipsosauri, B. polymyxa, B. mesentericus, B. megaterium, B. coagulans, B. vulgarus, B. halodurans, B. cereus*), *B. thermoamylovorans, Chromohalobacter* sp., *Halobacillus* sp., *Haloarcula hispanica, Halomonas meridiana*, the *Streptomyces* sp. (such as *Streptomyces coelicolor, Streptomyces lividans, Streptomyces rimosus*).

Fungal sources include, but are not limited to, *Aspergillus* sp. (such as *A. oryzae, A. kawachii, A. niger, A. awamori*, and *A. fumigatus*), *Penicillium* sp. (such as *P. brunneum, P. fellutanum, P. expansum, P. roquefortii*, and *P. chrysogenum*), and *Pycnoporus* sp. (such as *P. sanugineus* and *P. cinnabarinus*), *Talaromyces* sp. (such as *Talaromyces emersonii*).

The neutral metalloprotease, alkaline serine protease and/or amylase may also be obtained from genetically modified organisms or microorganisms mutated by chemical agents. The neutral metalloprotease, alkaline serine protease and/or amylase may be recombinant neutral metalloprotease, recombinant alkaline serine protease and/or recombinant amylase The neutral metalloprotease, alkaline serine protease and amylase may be produced by methods known in the art, including but not limited to, submerged fermentation and solid state fermentation.

The neutral metalloprotease, alkaline serine protease and amylase used in the present disclosure may be crude preparations or highly purified (such as that used in clinical and pharmaceutical industry). Purification methods commonly utilized include precipitation, chromatography (like ion exchange, gel filtration and affinity chromatography) and liquid-liquid extraction depending on the properties of the enzyme desired or the desired purity. The crude amylase enzyme may be obtained from a fermented mass by filtration and centrifugation. The crude amylase enzyme can be precipitated and concentrated using ammonium sulphate precipitation or organic solvents. The precipitated sample can be subjected to dialysis against water or a buffer for further concentration. This can be followed by any of the chromatographic techniques like ion exchange, gel filtration and affinity chromatography for further separation and purification of the enzyme.

Preferably, the amylase useful in the present disclosure is derived from the genome of *Bacillus* sp., preferably, *Bacillus amyloliquefaciens*.

An α-amylase or homolog thereof, is selected from the group consisting of: (i) an α-amylase comprising or consisting of the polypeptide of SEQ ID NO: 3; (ii) an α-amylase comprising or consisting of an amino acid sequence having at least 99%, at least 98%, at least 97%, at least 96%, at least 95%, at least 90%, at least 85%, or at least 80%, but less than 100%, identity to the polypeptide of SEQ ID NO: 3, (iii) an α-amylase encoded by a polynucleotide comprising or consisting of a nucleotide sequence having at least 99%, at least 98%, at least 97%, at least 96%, at least 95%, at least 90%, at least 85%, or at least 80%, but less than 100%, sequence identity to the polypeptide coding sequence of SEQ ID NO: 3, and (iv) an α-amylase encoded by a polynucleotide that hybridizes under low or high stringency conditions with the polypeptide coding sequence of SEQ ID NO: 3.

An α-amylase or homolog thereof, is selected from the group consisting of: (i) an α-amylase comprising or consisting of the polypeptide of SEQ ID NO: 6; (ii) an α-amylase comprising or consisting of an amino acid sequence having at least 99%, at least 98%, at least 97%, at least 96%, at least 95%, at least 90%, at least 85%, or at least 80%, but less than 100%, identity to the polypeptide of SEQ ID NO: 6, (iii) an α-amylase encoded by a polynucleotide comprising or consisting of a nucleotide sequence having at least 99%, at least 98%, at least 97%, at least 96%, at least 95%, at least 90%, at least 85%, or at least 80%, but less than 100%, sequence identity to the polypeptide coding sequence of SEQ ID NO: 6, and (iv) an α-amylase encoded by a polynucleotide that hybridizes under low or high stringency conditions with the polypeptide coding sequence of SEQ ID NO: 6.

The protease formulation/feed additive can be added to animal feed in either powder or liquid form.

In powdered form the composition of the feed additive is a low dust, dry blended and microgranulated enzyme powder derived from the natural fermentation of *Bacillus amyloliquefaciens* (see fermentation process described below) combined with a suitable carrier agent, including but not limited to, rice bran, cereal, pseudocereal, wheat flour and/or calcium sulphate dihydrate (Gypsum—$CaSO_4$) which is used to assist with mixing of the product in feed (see feed mixing and pelletization process conditions described below). This product is made from a natural raw material and as such may be subject to some batch to batch colour and/or odour variation, but these variations are not an indicator of enzyme activity and do not impact on product performance. The enzyme product maintains a combination of a neutral metalloprotease, serine alkaline protease and amylase activities in a specific ratio. This disclosure would describe the combination of protease activities mentioned above (metallo+serine) in a certain ratio with any type of amylase activities, e.g. Fungal amylase, Bacterial amylase, α-amylase, β-amylase, γ-amylase.

The protease enzyme formulation/additive would be comprised of 80-55% Metalloprotease [% of the total protease activity—as per the described analytical method—see below], and 20-45% serine protease [% of the total protease activity as per the described analytical method—see below]. The enzyme formulation/additive would be maintaining a protease:amylase ratio of 20:1.13, preferably 9:1.13, and more preferably 1:1.4. Most preferably, the protease:amylase ratio is 1:1.36.

According to a further aspect of the disclosure, a kit for supplementing animal feed is provided. The kit typically includes an enzyme combination comprising a neutral metalloprotease and a serine alkaline protease. The kit may also include an amylase, including not limited to, an amylase as described herein. Other components of the kit may include, but are not limited to, instructions to perform e addition of the protease combination or the protease mixture to n animal diet or animal feed, alone or with an amylase.

All references cited herein are hereby incorporated by reference in their entireties, whether previously specifically incorporated or not. As used herein, the terms "a", "an", and "any" are each intended to include both the singular and plural forms.

Having now fully described the disclosure, it will be appreciated by those skilled in the art that the same can be performed within a wide range of equivalent parameters, concentrations, and conditions without departing from the spirit and scope of the disclosure and without undue experimentation. While this disclosure has been described in connection with specific embodiments thereof, it will be understood that it is capable of further modifications. This application is intended to cover any variations, uses, or adaptations of the disclosure following, in general, the principles of the disclosure and including such departures from the present disclosure as come within known or customary practice within the art to which the disclosure pertains and may be applied to the essential features hereinbefore set forth.

EXAMPLES

Example 1

The experimental design was developed to assess the impact of the disclosure (at graded levels of concentrations) and a commercially available protease (Com.Prot D.) in a monogastric diet with reduced level of crude protein and digestible aminoacids to those required by the test animal (NC). The expectations from this design was to see a reduction in growth performance and feed efficiency of the tested animals receiving the NC diet and not supplemented with any protease in comparison to a formulation meeting all nutrient specifications (PC). With this confirmed response, the efficacy of the disclosure and the commercial protease (Com.Prot D) on restoring the growth performance of the tested animals was investigated.

Experimental design and levels of protease (and amylase) enzyme activity delivered in feed on a study for assessing the efficacy of the protease combination.

The total activity was measured using neutral protease activity (NPU).

In Table 1.1. the enzyme combination of the present disclosure (metalloprotease, serine protease+amylase) were compared to a commercial protease enzyme (Com.Prot.D). The commercial protease is a serine protease, only.

TABLE 1.1

| Description | | NPU U/kg Mash feed protease | pNP U/kg mash feed Protease | BAA U/kg mash feed Amylase |
| --- | --- | --- | --- | --- |
| T1 | Positive Control (PC) | — | — | — |
| T2 | Negative control (NC) – 7.5% AA + CP | — | — | — |
| T3 | Protease (14 g/mT) – 100 g/mT | 17,680 | 122 | 5,685 |
| T4 | Protease (22 g/mT) – 100 g/mT | 27,783 | 191 | 8,934 |
| T5 | Protease (360 g/mT) | 137,651 | 949 | 58,798 |
| T6 | Com. Prot D. (400 g/ml) | n/a | 918 | 0 |

T3, T4, and T5 are protease combinations of the present disclosure.

In addition, summary of growth performance results of a broiler chicken study assessing the efficacy of protease at graded doses in protein deficient diets in comparison to a formulation meeting birds nutrient requirements and a commercially available protease over a 42-day period.

TABLE 1.2

| | Description | BWG, g/bird | FI, g/bird | FCR, g/g | PI |
| --- | --- | --- | --- | --- | --- |
| T1 | Positive Control (PC) | 2727$^a$ | 4149$^a$ | 1.522$^d$ | 433$^a$ |
| T2 | Negative control (NC) – 7.5% AA + CP | 2540$^d$ | 4067$^{bc}$ | 1.601$^a$ | 384$^d$ |
| T3 | Protease (14 g/mT) – 100 g/mT | 2592$^{bc}$ | 4015$^c$ | 1.549$^c$ | 397$^{bc}$ |
| T4 | Protease (22 g/mT) – 100 g/mT | 2859$^{bc}$ | 4047$^{bc}$ | 1.563$^{bc}$ | 400$^b$ |
| T5 | Protease (360 g/mT) | 2562$^{cd}$ | 4059$^{bc}$ | 1.584$^{ab}$ | 389$^{cd}$ |
| T6 | Com.Prot D. (400 g/mT)] | 2621$^b$ | 4116$^{ab}$ | 1.570$^{bc}$ | 401$^b$ |
| | Pooled SEM | 9.153 | 10.534 | 0.004 | 2.388 |
| | p | <0.0001 | 0.0015 | <0.0001 | <0.0001 |

T3, T4, and T5 are protease combinations of the present disclosure.

Table 1.2 describes details of a feeding trial conducted to demonstrate the impact of said protease enzyme on BROILER GROWTH PERFORMANCE as measured through body weight gain (BWG) and Feed Conversation ratio (FCR).

Example 2

Figure 2A:
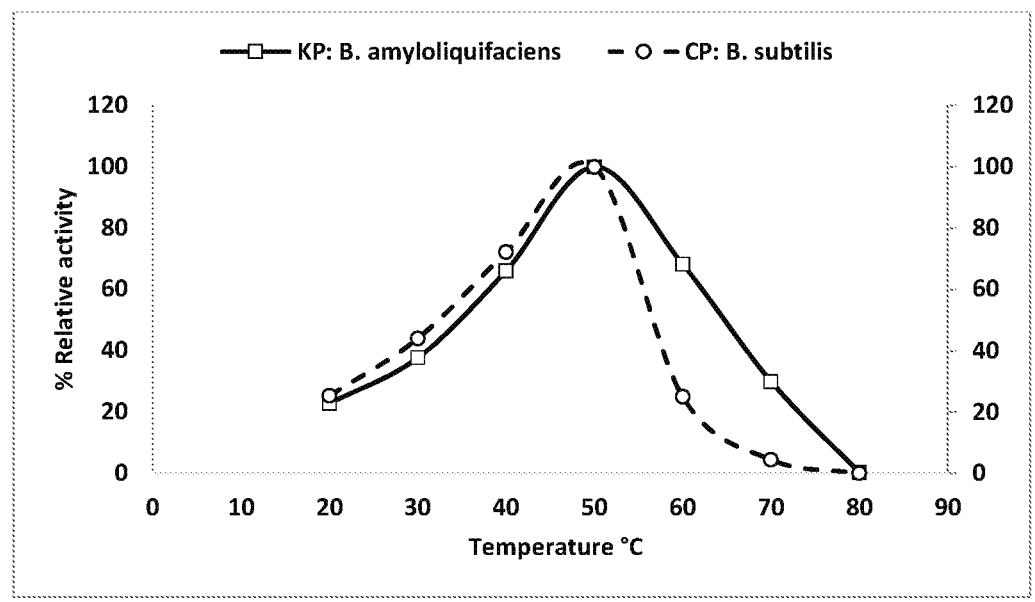
FIGS. 2A and 2B depict relative protease activity in response to temperature.
Figure 2B:
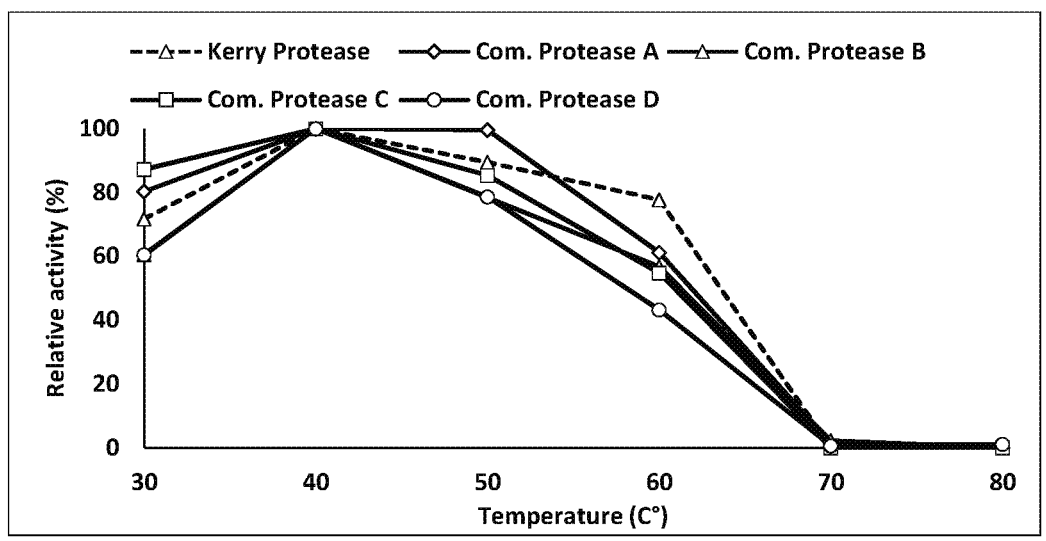
Figure 3A:
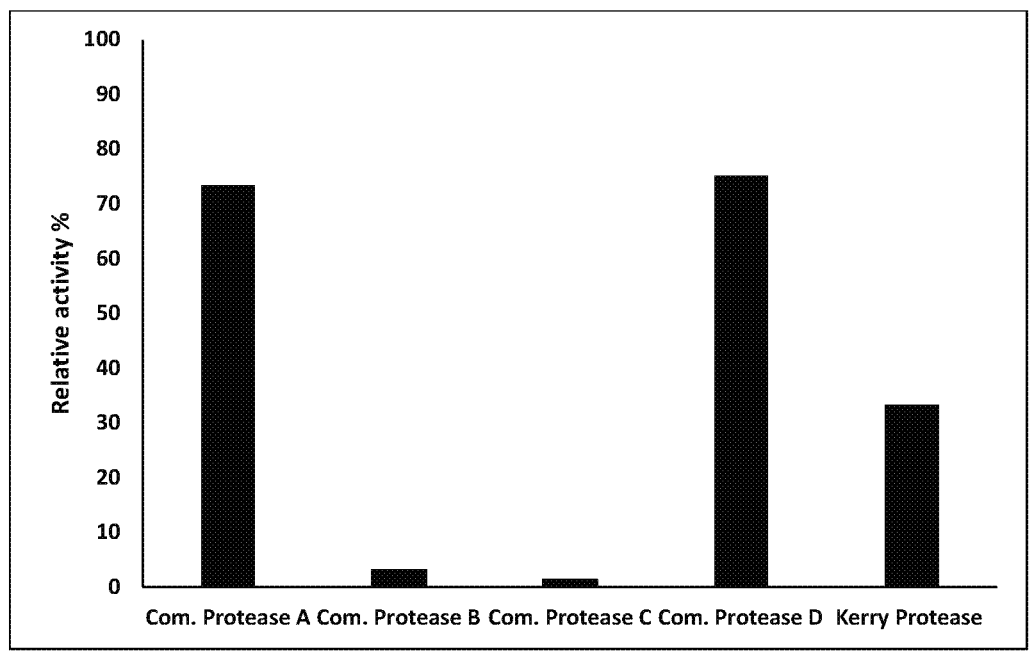
FIGS. 3A and 3B depict residual protease activity following exposure to acidic pH conditions (pH 3.5) for 30 minutes.
Figure 3B:
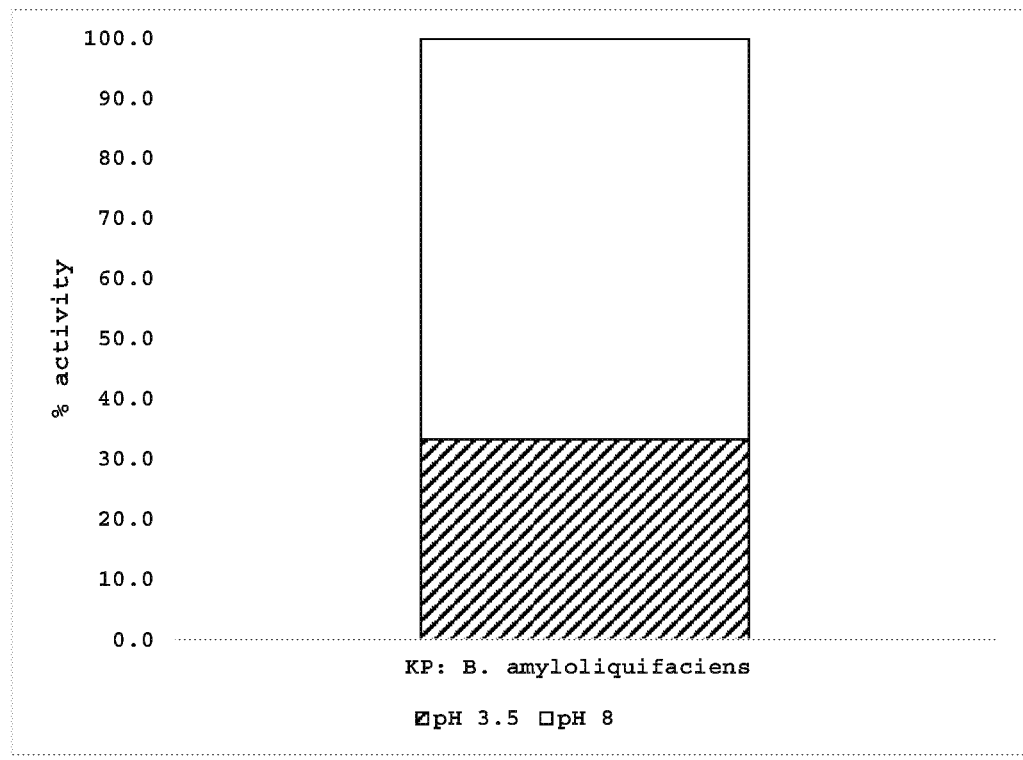

The protease enzyme combination described herein has the following characteristics in order to deliver its efficacy for improving digestibility of proteins as well as nutritional optimization of animal diets or feed:
  Maintaining optimal activity in the pH range between 7-10* (see FIG. 1)
  Maintaining optimal activity at temperatures ranging between 30-60° C.* (FIGS. 2A and 2B). The protease of the disclosure maintains at least 70% of activity at 60° C. under defined assay conditions (versus the optimum 40° C.) while most of other commercial proteases are clearly less active at 60° C. under said conditions
  pH stability: residual protease activity greater than 30% (of optimal, pH8) following exposure to acidic pH condition (pH 3.5) for 30 mins* (FIGS. 3A and 3B)
  Maintaining a protease:amylase ratio of 20:1.13, preferably 9:1.13, more preferably 1:1.4 (Table 1.3)
  Maintaining a ratio of metalloprotease:serine protease of X (Table 1.4)
The total activity was measured using pNP or neutral protease activity (NPU).

Protease activity determined using the pNP method was assayed at 37° C. using 5 mM N-Succinyl-Ala-Ala-Pro-Phe p-nitroanilide (SEQ ID NO: 7) as substrate and 100 mM Tris-HCl at pH 8. Protease enzyme catalysed the release of N-Succinyl-Ala-Ala-Pro-Phe p-nitroanilide to yield p-nitroaniline which is measured spectrophotometrically at 405 nm.

The neutral protease activity (NPU) was determined by a modified folin assay method where rate of hydrolysis is observed over a 10 minute incubation period at pH 7 and a temperature of 30° C.

Inactivation of individual proteases contained within enzyme mixtures, using selective inhibitors, is used for understanding compositional information (ratio of neutral metalloprotease:alkaline serine protease) pertaining to the types of protease activities contained in the protease feed additive.

Metal chelators such as ethylenediaminetetraacetic acid (EDTA) that sequesters zinc ions and inhibits the metalloprotease's activity, was used to inhibit the neutral metalloprotease in the enzyme combination to allow determination of serine protease activity.

Likewise, a potent inhibitor of the serine proteases such as phenyl methyl sulfonyl Fluoride (PMSF) which inactivates alkaline serine protease by binding to the serine residue in the active site of the enzyme, was used to inhibit the alkaline serine protease in the enzyme combination.

TABLE 1.3

Protease activities and Ratios of metalloprotease and serine protease of protease powders of the present disclosure.

| Samples name | Total Protease (NPU) | Metallo-Protease activity (w/PMSF) | Serine Protease activity (w/EDTA) | MP:SP ratio (NPU) | % Metallo Protease (NPU) | % Serine Protease (NPU) | BAA (U/g) | NPU:BAA |
|---|---|---|---|---|---|---|---|---|
| Protease (lot S1811139) BP16100701 | 315,658 (n = 3) (CV = 4%) | 239,738 (n = 2) (CV = 5%) | 89,850 (n = 1) | 3:1 | 72 | 24 | 163,329 | 1.93:1 |
| Protease S1907007BN 1156683 | 799,470 (n = 4) (CV = 4%) | 607,792 (n = 2) (CV = 5%) | 427,698 (n = 3) (CV = 7%) | 2.1:1 | 47 | 24 | 406,101 | 1.97:1 |
| Protease (BN 3492749) | 448,755 | 342,542 | 141,484 | 2.8:1 | 68 | 24 | 345,340 | 1.3:1 |

TABLE 1.4

Protease activities and Ratios of metalloprotease and serine protease of protease liquids of the present disclosure.

| Samples name | Total Protease (NPU) | Metallo-Protease activity (w/PMSF) | Serine Protease activity (w/EDTA) | MP:SP ratio (NPU) | % Metallo Protease (NPU) | % Serine Protease (NPU) | BAA (U/g) | NPU:BAA |
|---|---|---|---|---|---|---|---|---|
| protease (STB Liq [BN3493134] | 40,607 | 30,618 (n = 1) | 8,327 (n = 1) | 3.6:1 | 75 | 21 | 22,865 | 1.78:1 |
| Protease stb conc LIQ 20105147/ 3280944 | 34,988 | 28,117 | 12,384 | 3.25:1 | 65 | 20 | 11,560 | 3:1 |
| Protease stb conc LIQ 20105147/ 2719592 | 43,006 | 23,799 | 11,466 | 1.6:1 | 73 | 45 | 58,443 | 1:1.36 |
| Protease sterile filtered stabilised liquid 3766371 | 51,299 | 31,818 | 12,768 | 2:1 | 75 | 38 | 6,752 | 7.6:1 |
| Protease sterile filtered stabilised liquid 3766372 | 48,215 | 38,192 | 10,877 | 3.9:1 | 77 | 21 | 5,324 | 9:1 |

The invention claimed is:

1. A method for improving digestibility of proteins, comprising: administering to an animal a feed supplement comprising i) a protease combination or a protease mixture having neutral metalloprotease and serine alkaline protease activity and ii) amylase, wherein the protease combination has a ratio of total activity of neutral metalloprotease:serine alkaline protease of from 4:1 to 1.5:1,
the amylase is at least one selected from the group consisting of an α-amylase, a β-amylase, and a γ-amylase;
the protease combination or the protease mixture and amylase have a ratio of total activity of protease: amylase of from 20:1.13 to 1:5; and
the protease combination or the protease mixture is derived from *Bacillus amyloliquefaciens*.

2. A method of improving digestibility of proteins in animal feed, comprising: adding to the animal feed i) a protease combination having neutral metalloprotease and serine alkaline protease activity and ii) amylase, wherein the protease combination or the protease mixture has a ratio of total activity of neutral metalloprotease:serine alkaline protease of from 4:1 to 1.5:1,
the amylase is at least one selected from the group consisting of an α-amylase, a β-amylase, and a γ-amylase;
the protease combination or the protease mixture and amylase have a ratio of total activity of protease: amylase of from 20:1.13 to 1:5; and
the protease combination or the protease mixture is derived from *Bacillus amyloliquefaciens*.

3. A method of optimizing nutritional value of an animal diet or feed, comprising: adding to the animal diet or feed i) a protease combination having neutral metalloprotease and serine alkaline protease activity and ii) amylase, wherein the protease combination has a ratio of total activity of neutral metalloprotease:serine alkaline protease of from 4:1 to 1.5:1,
the amylase is at least one selected from the group consisting of an α-amylase, a β-amylase, and a γ-amylase;
the protease combination or the protease mixture and amylase have a ratio of total activity of protease: amylase of from 20:1.13 to 1:5; and
the protease combination or the protease mixture is derived from *Bacillus amyloliquefaciens*.

4. The method of claim 1, wherein the animal comprises poultry, swine, ruminant, amphibians, fish, reptiles, birds, or mammals.

5. The method of claim 4, wherein the animal is a monogastric animal comprising humans, primates, poultry, birds, swine, dogs, cats, or horses.

6. The method of any one of claims 1 to 3, wherein the protease combination or the protease mixture is in a feed additive or feed supplement.

7. The method of any one of claims 2 to 3, wherein the animal feed is provided to an animal comprising poultry, swine, ruminant, amphibians, fish, reptiles, birds or mammals.

8. The method of claim 7, wherein the animal is a monogastric animal comprising humans, primates, poultry, birds, swine, dogs, cats, or horses.

9. The method of claim 1, wherein the ratio of total activity of neutral metalloprotease and serine alkaline protease:amylase is 9:1.13.

10. The method of claim 1, wherein the ratio of total activity of neutral metalloprotease and serine alkaline protease:amylase is 1:1.36.

11. A feed additive or feed supplement, comprising:
a protease combination or a protease mixture having neutral metalloprotease, serine alkaline protease activity; and
an amylase,
wherein the neutral metalloprotease and serine alkaline protease have a ratio of total activity of neutral metalloprotease:serine alkaline protease of from 4:1 to 1.5:1;

the amylase is at least one selected from the group consisting of an α-amylase, a β-amylase, and a γ-amylase;

the protease combination or the protease mixture and amylase have a ratio of total activity of protease:amylase of from 20:1.13 to 1:5; and the protease combination or the protease mixture is derived from *Bacillus amyloliquefaciens*.

12. The feed additive or feed supplement of claim 11, wherein the ratio of total activity of neutral metalloprotease and serine alkaline protease:amylase is 9:1.13.

13. The feed additive or feed supplement of claim 11, wherein the ratio of total activity of neutral metalloprotease and serine alkaline protease:amylase is 1:1.36.

14. An enzyme composition, comprising:

a protease combination or a protease mixture having neutral metalloprotease and serine alkaline protease activity; and amylase, wherein the neutral metalloprotease and serine alkaline protease have a ratio of total activity of neutral metalloprotease:serine alkaline protease of from 4:1 to 1.5:1;

the amylase is at least one selected from the group consisting of an α-amylase, a β-amylase, and a γ-amylase;

the protease combination or the protease mixture and amylase have a ratio of total activity of protease:amylase of from 20:1.13 to 1:5; and the protease combination or the protease mixture is derived from *Bacillus amyloliquefaciens*.

15. The enzyme composition of claim 14, wherein the ratio of total activity of neutral metalloprotease and serine alkaline protease:amylase is 9:1.13.

16. The enzyme composition of claim 14, wherein the ratio of total activity of neutral metalloprotease and serine alkaline protease:amylase is 1:1.36.

17. The enzyme composition of claim 14, wherein the composition is in a feed formulation.

18. A kit for optimizing the nutritional value of an animal diet or animal feed, comprising:

(a) a protease enzyme combination or a protease enzyme mixture having neutral metalloprotease and serine alkaline protease activity, and an amylase, wherein:

the protease enzyme combination or the protease enzyme mixture has a ratio of total activity of neutral metalloprotease:serine alkaline protease of from 4:1 to 1.5:1, and the protease enzyme combination or the protease enzyme mixture and amylase have a ratio of total activity of neutral metalloprotease and serine alkaline protease:amylase of from 20:1.13 to 1:5; and (b) instructions to enable supplementation of the animal diet or the animal feed with the enzyme combination, the amylase is at least one selected from the group consisting of an α-amylase, a β-amylase, and a γ-amylase;

the protease combination or the protease mixture and amylase have a ratio of total activity of protease:amylase of from 20:1.13 to 1:5; and the protease combination or the protease mixture is derived from *Bacillus amyloliquefaciens*.

19. The kit of claim 18, wherein the ratio of total activity of neutral metalloprotease and serine alkaline protease:amylase is 9:1.13.

20. The kit of claim 18, wherein the ratio of total activity of neutral metalloprotease and serine alkaline protease:amylase is 1:1.36.

* * * * *